US007078046B1

(12) United States Patent
Rabe et al.

(10) Patent No.: US 7,078,046 B1
(45) Date of Patent: Jul. 18, 2006

(54) ELECTROSTATICALLY-SPRAYABLE TOPICAL COMPOSITIONS HAVING INSULATING EXTERNAL PHASE AND CONDUCTIVE INTERNAL PHASE

(75) Inventors: Thomas Elliot Rabe, Baltimore, MD (US); Helen Shu Ying Yen, Cockeysville, MD (US); June Turkanis Brennock, Cincinnati, OH (US); Caroline Becque Martello, Parkton, MD (US)

(73) Assignee: The Procter & Gamble Company, Cincinnati, OH (US)

( * ) Notice: Subject to any disclaimer, the term of this patent is extended or adjusted under 35 U.S.C. 154(b) by 245 days.

(21) Appl. No.: 09/629,734

(22) Filed: Jul. 31, 2000

Related U.S. Application Data

(63) Continuation-in-part of application No. 09/584,464, filed on May 31, 2000.

(60) Provisional application No. 60/149,566, filed on Aug. 18, 1999.

(51) Int. Cl.
*A61K 9/107* (2006.01)
*A61K 42/34* (2006.01)
*B05D 1/04* (2006.01)

(52) U.S. Cl. ........................ 424/401; 514/937; 516/20; 516/23; 427/475

(58) Field of Classification Search ............. 424/78.03, 424/63, 65, 69, 401; 514/844–48, 937; 516/20, 516/23; 427/475
See application file for complete search history.

(56) References Cited

U.S. PATENT DOCUMENTS

| | | | | |
|---|---|---|---|---|
| 3,012,969 A | | 12/1961 | van der Minne et al. | 252/153 |
| 4,079,894 A | | 3/1978 | Harjar et al. | 239/526 |
| 4,122,845 A | | 10/1978 | Stouffer et al. | 128/66 |
| 4,143,819 A | | 3/1979 | Hastings | 239/707 |
| 4,194,696 A | | 3/1980 | Harjar | 239/707 |
| 4,258,073 A | | 3/1981 | Payne | 427/1 |
| 4,776,515 A | | 10/1988 | Michalchik | 239/3 |
| 5,200,248 A | | 4/1993 | Thompson et al. | 428/131 |
| 5,222,663 A | | 6/1993 | Noakes et al. | 239/3 |
| 5,229,105 A | | 7/1993 | Wilmsmann | 424/59 |
| 5,268,166 A | | 12/1993 | Barnett et al. | 424/47 |
| 5,296,681 A | | 3/1994 | Tschauder | 219/410 |
| 5,322,684 A | | 6/1994 | Barnett et al. | 424/47 |
| 5,422,630 A | | 6/1995 | Quinn et al. | 340/661 |
| 5,468,488 A | | 11/1995 | Wahi | 424/78.03 |
| 5,494,674 A | * | 2/1996 | Barnett et al. | 424/400 |
| 5,505,937 A | | 4/1996 | Castrogiovanni et al. | 424/64 |
| 5,519,159 A | | 5/1996 | Narabe et al. | 558/169 |
| 5,662,890 A | | 9/1997 | Punto et al. | 424/59 |
| 5,674,481 A | | 10/1997 | Wahi | 424/78.03 |
| 5,800,816 A | | 9/1998 | Brieva et al. | 424/63 |
| 5,945,111 A | | 8/1999 | Esser | 424/401 |

FOREIGN PATENT DOCUMENTS

| | | | |
|---|---|---|---|
| BE | 882449 | | 7/1980 |
| BE | 882450 | | 7/1980 |
| EP | 0 096731 | | 12/1983 |
| EP | 0 523 960 | | 1/1993 |
| EP | 0 523 961 | | 1/1993 |
| EP | 0 523 962 | | 1/1993 |
| EP | 0 523 963 | | 1/1993 |
| EP | 0 523 964 | | 1/1993 |
| EP | 0 544 158 | | 6/1993 |
| FR | 2127433 | | 10/1972 |
| GB | 2 128 900 | | 5/1984 |
| GB | 2 273 673 | | 6/1994 |
| GB | 2 273 872 | | 7/1994 |
| GB | 2 291 804 | A | 2/1996 |
| GB | 2 319 177 | A | 5/1998 |
| JP | 56-097214 | | 8/1981 |
| JP | 05-192223 | A | 8/1993 |
| JP | 05-192224 | A | 8/1993 |
| JP | 05-194145 | A | 8/1993 |
| JP | 7-60166 | | 3/1995 |
| JP | 07/173031 | A | 7/1995 |
| JP | 10-146216 | | 6/1998 |
| SU | 867 927 | | 9/1981 |
| WO | WO 94/11119 | | 5/1994 |
| WO | WO 94/27560 | | 12/1994 |
| WO | WO 95/29758 | | 11/1995 |
| WO | WO 96/03964 | A1 | 2/1996 |
| WO | WO 96/10459 | | 4/1996 |
| WO | WO 96/11062 | | 4/1996 |
| WO | WO 97/04737 | A1 | 2/1997 |
| WO | WO 97/17057 | A1 | 5/1997 |
| WO | WO 97/33527 | | 9/1997 |
| WO | WO 98/26752 | A1 | 6/1998 |

OTHER PUBLICATIONS

Cook, T.H., et al., "Topographics of Dry Skn, Non-dry Skin, and Cosmetically Treated Dry Skin as Quantified by Skin Profilometry", J. Soc. Cosmet. Chem., vol. 36, pp. 143-152 (Mar./Apr. 1985).

Dorogi. P.L, et al., "Assessment of Skin Conditions Using Profilometry", Cosmetics & Toiletries, vol. 104, pp. 39-44 (Mar. 1989).

* cited by examiner

*Primary Examiner*—Edward J. Webman
(74) *Attorney, Agent, or Firm*—Vladimir Vitenberg; Dara M. Kendall; Darryl C. Little

(57) ABSTRACT

Disclosed are electrostatically-sprayable topical compositions, more particularly topical emulsion compositions, and methods of treating the skin by electrostatic application of such compositions. In one aspect the composition comprises an insulating external phase comprising one or more insulating materials and a conductive internal phase comprising one or more conductive materials. The compositions preferably also contain one or more particulate materials to be deposited on the skin, e.g., pigments, inert absorbents and the like.

21 Claims, No Drawings

ELECTROSTATICALLY-SPRAYABLE TOPICAL COMPOSITIONS HAVING INSULATING EXTERNAL PHASE AND CONDUCTIVE INTERNAL PHASE

CROSS REFERENCE TO RELATED APPLICATION

This application claims priority under Title 35, United States Code 119(e) from U.S. Provisional Application No. 60/149,566, filed on Aug. 18, 1999 and is a continuation-in-part application of U.S. application Ser. No. 09/584,464, filed May 31, 2000.

FIELD OF THE INVENTION

The present invention relates to electrostatically-sprayable topical compositions, more particularly topical emulsion compositions, and methods of treating the skin by electrostatic application of such compositions. Examples of electrostatically-sprayable compositions include color cosmetics and other skin care compositions.

BACKGROUND OF THE INVENTION

A variety of topically-applied skin treatment products are known. Typically, such products are applied by massaging or rubbing into the skin with the fingers or sponge-type applicator. Other methods of application are also known, including aerosol spraying, non-aerosol pump spraying, and electrostatic spraying. For example, electrostatic spraying of skin treatment agents is disclosed in U.S. Pat. No. 5,494,674, issued to Barnett et al. on Feb. 27, 1996.

Electrostatic spraying of topical materials has been proposed as a means for more efficient consumption and product activity, control over application, ease and cleanliness/hygiene of application, and even coverage.

In particular, the art has described electrostatically-sprayable formulations which comprise a single, semi-conductive phase which is accomplished by modifying the conductivity of typically insulating fluids by blending with conductive fluids like ethanol. Such systems are essentially continuous in regard to their electrical resistivity in that the conductive and insulating fluids form a single phase.

While a variety of topical compositions have been provided, there is an ongoing need to improve cosmetic compositions to impart good coverage yet a natural appearance. There is also an ongoing need to improve delivery of skin care compositions in a non-irritating and efficient manner. For example, it is desirable to administer topical skin care actives uniformly to the skin, so as to maximize efficacy. Furthermore, there is an ongoing need to maximize formulation capability in order to improve esthetic and/or functional properties of topical compositions.

The present invention relates to novel methods of treating the skin by electrostatically spraying a topical composition on the skin, wherein the composition comprises an emulsion having an insulating, external phase and a conductive, internal phase. That such compositions can be electrostatically sprayed is surprising since the art has heretofore described essentially electrically-continuous systems.

This surprising development allows for wider formulation of electrostatically sprayable systems. That is, the formulation of essentially electrically continuous systems is limited by the need to maintain the electrical continuity of the system. On the other hand, in the present invention it is possible to utilize different levels of polar and non-polarsoluble or dispersible materials to thereby improve the benefits of the composition. In addition, incorporation of such ingredients wherein the non-polar material, e.g., non-polar silicones or hydrocarbons, is in the external phase provides improved tactile sensation upon application and tends to reduce the irritation potential of volatile materials which may be incorporated into the internal phase. It is believed that the external, insulating phase insulates such potentially irritating materials from the skin while the product dries on the skin.

It has also been found that when powder materials (e.g., pigments) which are dispersible in the external phase, and not substantially in the internal phase, are incorporated into the emulsion, a "clustering" phenomena of powder results which makes the apparent droplet size (i.e., the droplet size perceived by the eye once the product has dried), smaller than the actual droplet size which is sprayed. Such smaller apparent droplet sizes tend to provide better integration of the product with the bare skin leading to a more natural look. This ability to integrate with the bare skin also enables the use of broader range of shade palettes while maintaining a natural appearance. In contrast, when pigments are incorporated into essentially single phase, semi-conductive compositions, the pigments are generally evenly distributed throughout the sprayed droplets. When such compositions are sprayed, the apparent droplet size approximates the droplet size actually sprayed.

SUMMARY OF THE INVENTION

The present invention relates to electrostatically-sprayable topical compositions, more particularly topical emulsion compositions, and methods of treating the skin by electrostatic application of such compositions.

In one aspect the present invention provides a topical emulsion composition which is electrostatically sprayable, the composition comprising an insulating external phase comprising one or more insulating materials and a conductive internal phase comprising one or more conductive materials. The compositions comprise a component for providing some esthetic or functional benefit to the skin, which may be the insulating, conductive or other material. Preferred compositions comprise one or more particulate materials such as pigments, oil absorbers and the like.

The electrostatically sprayable emulsion compositions preferably comprise:

a) from about 5% to about 75% of an insulating external phase comprising one or more insulating materials; and b) from about 15% to about 80% of a conductive internal phase comprising one or more conductive materials.

The compositions preferably comprise from about 5 to about 75% of insulating material and from about 15% to about 80% of conductive material. Preferred compositions comprise from about 0.1% to about 35% of one or more powders.

Another aspect of the invention provides a method of treating the skin by electrostatically spraying such compositions. The present invention also relates to instructions for applying the composition by electrostatic spray techniques and a method of training one how to self-apply the compositions by electrostatic spray techniques.

It has been found that the present invention provides one or more skin care benefits, including one or more of improved color integration with bare skin (providing a more natural appearance and enabling broader useable shade palettes for a given skin color), improved skin feel, and reduced potential for local irritation.

DETAILED DESCRIPTION OF THE INVENTION

The essential elements of the present invention are herein described below. Also included are non-limiting descriptions of various optional and preferred elements useful in the compositions of the present invention.

The present invention can comprise, consist of, or consist essentially of any of the required or optional components and/or limitations described herein.

In the description of the invention various embodiments and/or individual features are disclosed. As will be apparent for the skilled practitioner all combinations of such embodiments and features are possible and can result in preferred executions of the invention.

All percentages and ratios are calculated by weight unless otherwise indicated. All percentages are calculated based on the total composition unless otherwise indicated.

All component or composition levels are in reference to the active level of that component or composition, and are exclusive of impurities, for example, residual solvents or by-products, which may be present in commercially available sources.

Referred to herein are trade names for materials. The inventors herein do not intend to be limited by materials under a certain trade name. Equivalent materials (e.g., those obtained from a different source under a different name or catalog (reference) number) to those referenced by trade name may be substituted and utilized in the compositions herein.

The compositions described herein and their components are suitable for topical application, that is they are suitable for use in contact with human skin without undue toxicity, incompatibility, instability, allergic response, and the like within the scope of sound medical judgment.

Active and other ingredients useful herein may be categorized or described herein by their cosmetic, prophylactic and/or therapeutic benefit or their postulated mode of action. It is to be understood that the active and other ingredients useful herein can in some instances provide more than one cosmetic, prophylactic and/or therapeutic benefit or operate via more than one mode of action. Therefore, classifications herein are made for the sake of convenience and are not intended to limit an ingredient to the particularly stated application or applications listed.

All documents referred to herein, including all patents, patent applications, and printed publications, are hereby incorporated by reference in their entirety.

Compositions of the present invention are electrostatically sprayable, topical emulsion compositions comprising (i) an insulating, continuous external phase comprising one or more liquid insulating materials, and (ii) a conductive, discontinuous internal phase comprising one more conductive materials which may be in liquid or particulate form. The conductive internal phase exists as droplets or particles dispersed in the insulating external phase. The compositions comprise a component for providing some esthetic or functional benefit to the skin, which may be the insulating, conductive or other material.

The compositions hereof are electrostatically sprayable and are suitably directly applied to the skin by electrostatic spray techniques. In general, this method involves raising the composition to be sprayed to a sufficiently high electric potential in a spray nozzle to cause the composition to atomize as a spray of electrically charged droplets. The electrically charged droplets seek the closest earthed object to discharge their electric charge, which can be arranged to be the desired spray target.

In order to be electrostatically sprayable, a composition must have a resistivity which enables atomization as a spray of the charged droplets. In preferred compositions, the components of the composition are selected or adjusted such that the composition has a resistivity of from about 0.01 to about 5000 Mega-ohm-cm, more preferably from about 0.01 to about 2000 Mega-ohm-cm, most preferably from about 0.1 to about 500 Mega-ohm-cm. Resistivity is measured using standard, conventional apparatus and methods, generally at 25 degree C. Resistivity can be adjusted as necessary by varying the relative levels of insulating materials and conductive materials. In general, resistivity decreases with increasing percentage of conductive materials and decreasing percentage of insulating materials.

The compositions must also have a viscosity which permits electrostatically spraying. Materials of a wide range of viscosities may be suitable for use in the present invention, however the viscosity is preferably sufficiently high to minimize wicking of the composition droplets as they are applied to the skin. The tendency to wick depends on the surface tension of the composition and tends to increase with decreasing surface tension of the liquid components. In compositions based on liquid components having a relatively low surface tension (i.e., which have a tendency to wet the substrate), it is generally desirable to utilize a viscosity increasing agent to minimize wicking such as the structuring agents or thickeners described herein. Preferably the viscosity is in the range of from about 0.1 to about 50,000 mPas, more preferably from about 0.5 to about 20,000 mPas, most preferably from about 5 to about 10,000 mPas (at 25 degree C., using 60 mm parallel plate with 0.5 mm gap at rate of 10 $sec^{-1}$).

Insulating External Phase

The insulating external phase comprises one or more insulating materials such that the insulating phase as a whole would not be suitable for electrostatic spraying (that is, it would not be able to cause sufficient alignment of the dipole molecules in the field to result in the subsequent, necessary net force). This phase preferably has a resistivity of about 2000 Mega-ohm-cm or more, more preferably about 5000 Mega-ohm-cm or more. This phase is fluid and comprises at least one insulating liquid material, preferably having a viscosity of about 10,000 mPas or less.

Suitable insulating materials are selected from non-polar substances, e.g. oils and other hydrophobic materials. The insulating materials may be volatile (i.e., having a measurable vapor pressure at 1 atm) or non-volatile, or mixtures of volatiles and non-volatiles, although volatile materials are preferred. Preferred liquid insulating materials have a viscosity of about 10,000 mPas or less. In addition to the at least one liquid insulating material, the composition may comprise non-liquid insulating materials. Preferred insulating materials are selected from the group consisting of volatile silicones, volatile hydrocarbons, and mixtures thereof.

Suitable volatile silicones include cyclic polyalkylsiloxanes represented by the chemical formula $[SiR_2—O]_n$ wherein R is an alkyl group (preferably R is methyl or ethyl, more preferably methyl) and n is an integer from about 3 to about 8, more preferably n is an integer from about 3 to about 7, and most preferably n is an integer from about 4 to about 6. When R is methyl, these materials are typically referred to as cyclomethicones. Commercially available cyclomethicones include Dow Corning® 244 fluid having a viscosity of 2.5 centistokes, and a boiling point of 172° C., which primarily contains the cyclomethicone tetramer (i.e. n=4), Dow Corning® 344 fluid having a viscosity of 2.5 centistokes and a boiling point of 178° C., which primarily contains the cyclomethicone pentamer (i.e. n=5), Dow Corning® 245 fluid having a viscosity of 4.2 centistokes and a boiling point of 205° C., which primarily contains a mixture of the cyclomethicone tetramer and pentamer (i.e. n=4 and 5), and Dow Corning® 345 fluid having a viscosity of 4.5 centistokes and a boiling point of 217°, which primarily contains a mixture of the cyclomethicone tetramer, pentamer, and hexamer (i.e. n=4, 5, and 6). Dow Corning® 244 fluid and Dow Corning® 344 fluid are preferred cyclomethicones.

Other suitable volatile silicones are linear polydimethyl siloxanes having from about 3 to about 9 silicon atoms and the general formula $(CH_3)_3$ Si—O—[—Si $(CH_3)_2$—O—]—$_n$—Si $(CH_3)_3$ where n=0–7. These silicones are available from various sources including Dow Corning Corporation and General Electric.

Suitable volatile hydrocarbons include those having boiling points in the range of 60–260° C., more preferably hydrocarbons having from about $C_8$ to about $C_{20}$ chain lengths, most preferably $C_8$ to $C_{20}$ isoparaffins. Preferred isoparaffins are isododecane, isohexadecane, isoeocosane, 2,2,4-trimethylpentane, 2,3-dimethylhexane and mixtures thereof, isododecane, isohexadecane, isoeocosane, and mixtures thereof being more preferred. Most preferred is isododecane, for example available as Permethyl 99A from Permethyl Corporation. Additionally, nonvolatile insulating materials can include nonvolatile oils, silicone, or hydrocarbon based materials. These materials can be naturally or synthetically derived, such as mineral oil and isoeicosane. Nonvolatile hydrocarbons may have a chain length ranging from C20 to C200. When used in the phase, nonvolatile insulting solvents typically range from 0.01% to 80% in the formulation.

Examples of non-volatile insulating materials suitable for use herein include non-volatile oils such as described in U.S. Pat. Nos. 5,800,816 and 5,505,937.

Conductive Internal Phase

The conductive internal phase comprises one or more electrically conductive materials such that the composition as a whole can, when in the presence of a non-uniform electric field, generate dielectrophoretic forces great enough to pull the composition toward the region of highest field intensity (hence creating an electrostatic spray). The conductive internal phase preferably has a resistivity of less than 5000 Mega-ohm-cm, more preferably less than about 2000 Mega-ohm-cm, most preferably less than about 500 Mega-ohm-cm. This phase preferably also has a relaxation time which is sufficiently long to enable a spray wherein all of the droplets have a size of less than 300 microns by standard light microscopy techniques. The conductive internal phase preferably has a relaxation time of from about 1E-7 to 1 seconds, more preferably from about 1E-6 to 1E-2 seconds, most preferably from about 1E-5 to 1E-3 seconds. The conductive internal phase exists as droplets or particles dispersed in the insulating external phase.

The electrically conductive materials comprise one or more polar substances. The conductive materials may be liquid or non-liquid (e.g., solid particles), and volatile or non-volatile, although volatile liquid materials are preferred. Suitable solid particles include metal powders, particles coated with metal or other conductive material, charged species (e.g., salts such as NaCl, or salts used conventionally in buffers in personal care products), and hydrophilic coated polymeric particles. Suitable liquids include polar solvents, polar aprotic solvents, glycols, polyols and mixtures thereof. Preferred conductive materials are selected from the group consisting of water, alcohols, glycols, polyols, ketones, solid particles, and mixtures thereof, more preferably alcohols, glycols, polyols (typically comprising about 16 or less carbon atoms) and mixtures thereof. More preferred conductive materials are propylene glycol, butylene glycol, dipropylene glycol, phenyl ethyl alcohol, ethanol, isopropyl alcohol, glycerin, 1,3-butanediol, 1,2-propane diol, isoprene glycol, acetone, water, or a mixture thereof. Particularly preferred conductive materials are propylene glycol, butylene glycol, ethanol, glycerin, water, or a mixture thereof. The conductive material of the internal phase is more preferably selected from propylene glycol, ethanol, and mixtures thereof, and is most preferably propylene glycol.

The compositions hereof are more preferably non-aqueous or contain only a small amount of water, e.g., less than about 10% by weight, preferably less than about 5% by weight, even more preferably less than about 1% by weight water. This is because, due to its short relaxation time and low resistivity, compositions containing large amounts of water generally create sprays which are difficult to control in terms of droplet size and spacing when electrostatic means are used.

The relative levels of the external phase and internal phase may vary, provided that sufficient conductive internal phase is present such that the composition realizes the electrical potential during spraying. The compositions preferably comprise (i) from about 5% to about 75%, more preferably from about 15% to about 70%, most preferably from about 20% to about 60%, of the insulating external phase and (ii) from about 15% to about 80%, more preferably from about 20% to about 75%, most preferably from about 30% to about 70% of the conductive internal phase. In general, sprayability improves with the level of conductive internal phase such that it will normally be advantageous to maximize the level of conductive phase. Preferred compositions comprise a weight ratio of insulating external phase to conductive internal phase (disregarding any non-conductive particulate materials) of from about 0.2:1 to about 8:1, more preferably about 1:1.

Optional Components

The compositions hereof comprise a component for providing some esthetic or functional benefit to the skin, e.g., sensory benefits relating to appearance, smell, or feel, therapeutic benefits, or prophylactic benefits. As will be recognized by the artisan having ordinary skill in the art, the above-described materials may themselves provide such benefits. In addition, the present compositions may comprise a variety of other ingredients such as are conventionally used in topical products.

The CTFA Cosmetic Ingredient Handbook, Second Edition (1992) describes a wide variety of nonlimiting cosmetic and pharmaceutical ingredients commonly used in the skin care industry, which are suitable for use in the topical compositions of the present invention. Such other materials may be dissolved or dispersed in the external and/or internal phase, depending on the relative solubilities of the components of the composition.

Compositions of the present invention are preferably generally liquid in form. Any adjunct materials which are present may be liquid, solid or semi-solid at room temperature, though they should be selected so not to deprive the composition of being electrostatically sprayable. For enhancing electrostatic spraying, preferred compositions have a solids content of about 35 weight % or less. In this regard, solids refers to particulate materials which are not soluble or miscible in the composition, and includes particulate pigments and oil absorbers.

Examples of suitable topical ingredient classes include: anti-acne agents, anti-inflammatory agents, anti-cellulite agents, anti-microbial agents, anti-fungal actives, antioxidants, radical scavengers, chelating agents, desquamation actives, skin bleaching and lightening agents, shine providing agents, shine control materials, skin-conditioning agents (e.g., humectants, including miscellaneous and occlusive), skin-feel agents, moisturizers, skin repair ingredients including agents for preventing, retarding, and/or reversing skin lines, wrinkles, or atrophy, skin soothing and/or healing agents, self-tanning actives, sunscreens, sunblocks, vitamins and derivatives thereof, abrasives, oil absorbents, astringents, skin sensates, film formers or materials, e.g., polymers, for aiding the film-forming properties and/or substantivity of the composition, including materials which impart extended wear and/or transfer resistance to the composition, colorants, dyes, opacifying agents, pigments, light scattering particles, essential oils, fragrance, anti-caking agents, antifoaming agents, binders, buffering agents, bulking agents, denaturants, pH adjusters, propellants, reducing agents, sequestrants, thickeners, structuring agents, emulsifiers, solubilizing agents, cosmetic biocides, and preservatives.

Preferred compositions of the invention comprise one or more ingredients selected from the group consisting of materials which impart transfer or wear resistant properties, powders, emulsifiers, structuring or thickening agents and mixtures thereof. Nonlimiting examples of these components include the following:

Materials for enhancing wear or transfer resistance. One or more materials for imparting film forming or substantive properties may be used in the present compositions, e.g., to provide long wear and/or transfer resistant properties. Such materials are typically used in an amount of from about 0.5% to about 20%.

Such materials include film forming polymeric materials. While the level of film forming polymeric material may vary, typically the film forming polymeric material is present in levels of from about 0.5% to about 20% by weight (e.g., from about 1 to about 15%), preferably from about 0.5% to about 10% by weight, more preferably from about 1% to about 8% by weight.

The film forming polymeric material may be soluble or dispersible in the internal or external phase, however in a preferred embodiment it is soluble or dispersible in the external phase. Preferred polymers form a non-tacky film which is removable with water used with cleansers such as soap.

Examples of suitable film forming polymeric materials include:

a) sulfopolyester resins, such as AQ sulfopolyester resins, such as AQ29D, AQ35S, AQ38D, AQ38S, AQ48S, and AQ55S (available from Eastman Chemicals);
b) polyvinylacetate/polyvinyl alcohol polymers, such as Vinex resins available from Air Products, including Vinex 2034, Vinex 2144, and Vinex 2019;
c) acrylic resins, including water dispersible acrylic resins available from National Starch under the trade name "Dermacryl", including Dermacryl LT;
d) polyvinylpyrrolidones (PVP), including Luviskol K17, K30 and K90 (available from BASF), water soluble copolymers of PVP, including PVP/VA S-630 and W-735 and PVP/dimethylaminoethylmethacrylate Copolymers such as Copolymer 845 and Copolymer 937 available from ISP, as well as other PVP polymers disclosed by E. S. Barabas in the *Encyclopedia of Polymer Science and Engineering,* 2 Ed. Vol. 17 pp. 198–257;
e) high molecular weight silicones such as dimethicone and organic-substituted dimethicones, especially those with viscosities of greater than about 50,000 mPas;
f) high molecular weight hydrocarbon polymers with viscosities of greater than about 50,000 mPas;
g) organosiloxanes, including organosiloxane resins, fluid diorganopolysiloxane polymers and silicone ester waxes.

Examples of these polymers and cosmetic compositions containing them are found in PCT publication Nos. WO96/33689, published Oct. 31, 1996; WO97/17058, published May 15, 1997; and U.S. Pat. No. 5,505,937 issued to Castrogiovanni et al. Apr. 9, 1996, all incorporated herein by reference. Additional film forming polymers suitable for use herein include the water-insoluble polymer materials in aqueous emulsion and water soluble film forming polymers described in PCT publication No. WO98/18431, published May 7, 1998, incorporated herein by reference. Examples of high molecular weight hydrocarbon polymers with viscosities of greater than about 50,000 mPas include polybutene, polybutene terephthalate, polydecene, polycyclopentadiene, and similar linear and branched high molecular weight hydrocarbons.

Preferred film forming polymers include organosiloxane resins comprising combinations of $R_3SiO_{1/2}$ "M" units, $R_2SiO$ "D" units, $RSiO_{3/2}$ "T" units, $SiO_2$ "Q" units in ratios to each other that satisfy the relationship $R_nSiO_{(4-n)/2}$ where n is a value between 1.0 and 1.50 and R is a methyl group. Note that a small amount, up to 5%, of silanol or alkoxy functionality may also be present in the resin structure as a result of processing. The organosiloxane resins must be solid at about 25° C. and have a molecular weight range of from about 1,000 to about 10,000 grams/mole. The resin is soluble in organic solvents such as toluene, xylene, isoparaffins, and cyclosiloxanes or the volatile carrier, indicating that the resin is not sufficiently crosslinked such that the resin is insoluble in the volatile carrier. Particularly preferred are resins comprising repeating monofunctional or $R_3SiO_{1/2}$ "M" units and the quadrafunctional or $SiO_2$ "Q" units, otherwise known as "MQ" resins as disclosed in U.S. Pat. No. 5,330,747, Krzysik, issued Jul. 19, 1994, incorporated herein by reference. In the present invention the ratio of the "M" to "Q" functional units is preferably about 0.7 and the value of n is 1.2. Organosiloxane resins such as these are commercially available such as Wacker 803 and 804 available from Wacker Silicones Corporation of Adrian Michigan, and G. E. 1170-002 from the General Electric Company.

Other materials for enhancing wear or transfer resistance include trimethylated silica. Suitable silicas of this type and cosmetic compositions containing them are described in U.S. Pat. No. 5,800,816 issued to Brieva et al., incorporated herein by reference.

Emulsifiers. The compositions hereof preferably contain one or more emulsifiers, e.g., to enhance the formation and stability of the emulsion. Compositions of the invention typically comprise from about 0.5% to about 10%, preferably from about 1% to about 5%, more preferably from about 1.5% to about 3% of one or more emulsifiers.

The hydrophilic-lipophilic balance value of the emulsifier (herein referred to as HLB) is chosen so as to optimally lower the interfacial tension between two phases of significantly different surface tension. Emulsifiers having an HLB ranging from about 4 to about 8 are preferred for use herein. HLB factors are described in Wilkinson and Moore, *Harry's Cosmeticology,* 7th Ed. 1982, p. 738. and Schick and Fowkes, Surfactant Science Series, Vol. 2, *Solvent Properties of Surfactant Solutions*, p 607, incorporated herein by reference. Exemplary emulsifiers include those disclosed in the C.T.F.A. Cosmetic Ingredient Handbook, 3rd Ed., Cosmetic and Fragrance Assn., Inc., Washington D.C. (1982) pp. 587–592; and Remington's Pharmaceutical Sciences, 15th Ed. 1975, pp. 335–337; and McCutcheon's Volume 1, *Emulsifiers & Detergents,* 1994, North American Edition, pp. 236–239; all herein incorporated by reference.

Particularly useful emulsifiers for the present compositions include polydiorganosiloxane-polyoxyalkylene copolymers. Such polymers are described in U.S. Pat. No. 4,268,499, incorporated herein by reference. Suitable copolymers of this type are known and many are available commercially. A preferred emulsifier of this type is known by its CTFA designation as dimethicone copolyol. Preferred emulsifiers also include the surfactants disclosed in U.S. Pat. No. 5,143,722, incorporated herein by reference.

Another preferred class of emulsifiers are high molecular weight polymeric emulsifiers such as are effective for stabilizing glycol/polyol-in-hydrocarbon systems (e.g., Arlacel P135 commercially available from Unichema).

Powders. The compositions hereof may comprise one or more powder materials, which are generally defined as dry, particulate matter having a particle size of from 0.001 to 150 microns, preferably 0.01 to 100 microns. The powder materials may be colored or non-colored (e.g., white or essentially clear), and may provide one or more benefits to the composition or skin such as coloration, light diffraction, oil absorption, translucency, opacification, pearlescence, matte appearance, lubricious feel, skin coverage and the like. These materials are well known in the art and are commercially available. Selection of the type and level of a given powder material for a particular purpose in a given product is within the skill of the artisan. Preferred ranges of non-conductive particulate matter are about 0.1 to about 35% of the total composition.

Suitable powders include various organic and inorganic pigments which color the composition or skin. Organic pigments are generally various types including azo, indigoid, triphenylmethane, anthraquinone, and xanthine dyes which are designated as D&C and FD&C blues, browns, greens, oranges, reds, yellows, etc. Inorganic pigments are generally insoluble metallic salts of certified color additives, referred to as lakes or iron oxides. Suitable pigments include those generally recognized as safe, and listed in C.T.F.A. *Cosmetic Ingredient Handbook*, First Edition, Washington D.C. (1988, incorporated herein by reference. Specific examples are red iron oxide, yellow iron oxide, black iron oxide, brown iron oxide, ultramarine, FD&C Red, Nos. 2, 5, 6, 7, 10, 11, 12, 13, 30 and 34; FD&C Yellow No. 5, Red 3, 21, 27, 28, and 33 Aluminum Lakes, Yellow 5, 6, and 10 Aluminum Lakes, Orange 5 Aluminum Lake, Blue 1 Aluminum Lake, Red 6 Barium Lake, Red 7 Calcium Lake, and the like.

Other useful powder materials include talc, mica, titanated mica (mica coated with titanium dioxide), iron oxide titanated mica, magnesium carbonate, calcium carbonate, magnesium silicate, silica (including spherical silica, hydrated silica and silica beads), titanium dioxide, zinc oxide, nylon powder, polyethylene powder, ethylene acrylates copolymer powder, methacrylate powder, polystyrene powder, silk powder, crystalline cellulose, starch, bismuth oxychloride, guanine, kaolin, chalk, diatomaceous earth, microsponges, boron nitride and the like. Additional powders useful herein are described in U.S. Pat. No. 5,505,937 issued to Castrogiovanni et al. Apr. 9, 1996.

Of the components useful as a matte finishing agents, low luster pigment, talc, polyethylene, hydrated silica, kaolin, titanium dioxide, titanated mica and mixtures thereof are preferred.

Micas, boron nitride and ethylene acrylates copolymer (e.g., EA-209 from Kobo) are preferred for imparting optical blurring effects through light diffraction and improving skin feel, e.g., by providing a lubricious feel. Another particulate material for improving skin feel is SPCAT 12 (a mixture of talc, polyvinylidene copolymer and isopropyl titanium triisostearate).

Preferred powders for absorbing oil are spherical, nonporous particles, more preferably having a particle size less than 25 microns. Examples of some preferred oil absorbing powders are Coslin C-100 (a spherical oil absorber commercially available from Englehard), Tospearl (spherical silica commercially available Kobo Industries), ethylene acrylates copolymer such as noted above, and SPCAT 12.

The powders may be surface treated with one or more agents, e.g., with lecithin, amino acids, mineral oil, silicone oil, or various other agents, which coat the powder surface, for example, to render the particles hydrophobic or hydrophilic. Such treatment may be preferred to improve ease of formulation and stability. Hydrophobically treated powders are preferred in the present compositions, since they are more easily dispersed in the external phase. Where the external phase comprises silicone, preferred hydrophobic powder treatments include polysiloxane treatments such as those disclosed in U.S. Pat. No. 5,143,722, incorporated herein by reference.

It is generally preferred that the conductive internal phase and insulating external phase have different affinities for powders or skin active materials to be deposited on the skin. More preferably, such materials are not dispersible or soluble in the internal phase. For example, a preferred composition comprises a relatively polar and/or high viscosity conductive fluid with relatively non-polar pigments. Without intending to be bound or limited by theory, it is believed that such incompatibility creates voids within a sprayed droplet which result in smaller clusters of pigments within a sprayed droplet, which in turn give the appearance of smaller droplets than what is actually sprayed (that is, the apparent droplet size is smaller than the actual sprayed droplet size). In general, it will therefore be desirable to select pigments and conductive materials such that the pigments are minimally wetted by the conductive internal phase.

In a preferred embodiment the composition is in the form of a cosmetic foundation. As used hereinafter, the term "foundation" refers to a liquid or semi-liquid skin cosmetic which includes, but is not limited to lotions, creams, gels, pastes, and the like. Typically the foundation is used over a large area of the skin, such as over the face, to provide a particular look. Foundation compositions of the invention typically comprise from about 2% to about 20% pigment for coloration, and from about 2% to about 15% of additional non-pigmented particulates.

Structuring or thickening agents. Compositions hereof preferably comprise one or more structuring or thickening agents, e.g., to enhance the stability of the composition, preferably upon exposure to the electric field applied during spraying. Preferred agents of this type are those which provide thickening or structure to the external phase. The compositions hereof may comprise from about 0.5% to about 50% of such agents.

Suitable structuring or thickening agents can be selected from the group consisting of silicones, waxes, clays, silicas, salts, natural and synthetic esters, fatty alcohols, and mixtures thereof. Nonlimiting examples of these structuring or thickening agents are described below.

Suitable silicones include alkyl siloxane gellants, high molecular weight dimethicones (fluids greater than 1000 mpas), and high molecular weight alkyl, hydroxyl, carboxyl, amino, and/or fluoro-substituted dimethicones (fluids greater than 1000 mPas). Preferred silicone gellants are described in U.S. Pat. Nos. 5,654,362 and 5,880,210, and include cyclomethicone and dimethicone crosspolymers (e.g., Dow Corning 9040).

Waxes can be defined as lower-melting organic mixtures or compounds of high molecular weight, solid at room temperature and generally similar in composition to fats and oils except that they contain no glycerides. Some are hydrocarbons, others are esters of fatty acids and alcohols. Suitable waxes may be selected from the group consisting of natural waxes including animal waxes, vegetable waxes, and mineral waxes, and synthetic waxes including petroleum waxes, ethylenic polymers, hydrocarbon waxes (e.g., Fischer-Tropsch waxes), ester waxes, silicone waxes, and mixtures thereof. Synthetic waxes include those disclosed in Warth, *Chemistry and Technology of Waxes*, Part 2, Reinhold Publishing (1956); herein incorporated by reference.

Specific examples of waxes include beeswax, lanolin wax, shellac wax, carnauba, candelilla, bayberry, jojoba esters, behenic acid waxes (e.g., glyceryl behenate which is available from Gattifosse as Compritol®), ozokerite, ceresin, paraffin, microcrystalline waxes, polyethylene homopolymers, polymers comprising ethylene oxide or ethylene (e.g., long chained polymers of ethylene oxide combined with a dihydric alcohol, namely polyoxyethylene glycol, such as Carbowax available from Carbide and Carbon Chemicals company; long-chained polymers of ethylene with OH or another stop length grouping at end of chain, including Fischer-Tropsch waxes as disclosed in *Warth*, supra, at pages 465–469 and specifically including Rosswax available from Ross Company and PT-0602 available from Astor Wax Company), $C_{24-45}$ alkyl methicones, $C_8$ to $C_{50}$ hydrocarbon waxes, alkylated polyvinyl pyrrolidones (e.g., "Ganex" alkylated polyvinylpyrrolidines available from the ISP Company), fatty alcohols from C20 to C60 (e.g., "Unilins", available from Petrolite Corporation) and mixtures thereof.

Preferred structuring or thickening agents are those which are substantially inert to distribution of charge through a fluide, e.g., waxes and high molecular weight silicones and hydrocarbons. For example, Versagel from Penreco can be used and is a high molecular weight material.

Water dispersible and oil dispersible clays may be useful to provide structure or thickening to the internal or external phase. Suitable clays can be selected, e.g., from montmorillonites, bentonites, hectorites, attapulgites, sepiolites, laponites, silicates and mixtures thereof.

Suitable water dispersible clays include bentonite and hectorite (such as Bentone EW, LT from Rheox); magnesium aluminum silicate (such as Veegum from Vanderbilt Co.); attapulgite (such as Attasorb or Pharamasorb from Engelhard, Inc.); laponite and montmorillonite (such as Gelwhite from ECC America); and mixtures thereof.

Oil-dispersible clays are preferred. Suitable oil dispersible clays include organophilically modified bentonites, hectorites and attapulgites. Specific commercially available examples of these clays include Bentone 34 (Rheox Corp.)—Quaternium-18 Bentonite; Tixogel VP (United Catalysts)—Quaternium-18 Bentonite; Bentone 38 (Rheox Corp.)—Quaternium-18 Hectorite; Bentone SD-3 (Rheox Corp.)—Dihydrogenated Tallow Benzylmonium Hectorite; Bentone 27 (Rheox Corp.)—Stearalkonium Hectorite; Tixogel LG (United Catalysts)—Stearalkonium Bentonite; Claytone 34 (Southern Clay) Quaternium-18 Bentonite; Claytone 40 (Southern Clay) Quaternium-18 Bentonite; Claytone AF (Southern Clay) Stearalkonium Bentonite; Claytone APA (Southern Clay) Stearalkonium Bentonite; Claytone GR (Southern Clay) Quaternium-18/Benzalkonium Bentonite; Claytone HT (Southern Clay) Quaternium-18/Benzalkonium Bentonite; Claytone PS (Southern Clay) Quaternium-18/Benzalkonium Bentonite; Claytone XL (Southern Clay) Quaternium-18 Bentonite; and Vistrol 1265 (Cimbar)-Organophilic Attapulgite. These organophilic clays can be purchased as pre-dispersed organophilic clay in either an oil or an organic solvent. The materials are in the form of a heavy paste that can be readily dispersed into the formulation. Such materials include Mastergels by Rheox, United Catalysts, and Southern Clay.

Other structuring or thickening agents include fumed silicas and alkali metal or ammonium halides. Examples of fumed silicas include Aerosil 200, Aerosil 300 and the alkyl-substituted fumed silicas such as the Aerosil R-100, 200, 800, and 900 series of materials, all available from the DeGussa Corporation.

Preferred structuring or thickening agents are those which are substantially inert to the distribution of charge through a fluid, e.g., waxes and high molecular weight silicones and hydrocarbons.

Product Forms and Particular Compositions

The compositions of the invention can be adapted to a variety of product forms, including pigmented and non-pigmented skin care compositions, e.g., lotions, creams, moisturizers, foundations, blush, eye shadow, self-tanning products, touch-up products (e.g., for oil/shine control), and chemical peels. Such compositions may comprise a volatile insulating and conductive material, one or more powders and/or skin treatment actives, and optionally one or more of the above described additional materials. Lotions, creams and moisturizers will typically include one or more of humectant, nonvolatile oil, emulsifier, preservative, powder material, and structuring agent or thickener. Examples of nonvolatile oils are described in U.S. Pat. No. 5,800,816. Such compositions may also comprise an effective amount of a prophylactic or therapeutic skin ingredient care ingredient, e.g., selected from oil/shine control actives, desquamation actives, anti-acne actives, anti-inflammatory actives, skin bleaching or lightening actives, skin-feel agents, skin repair ingredients, sunscreens, sunblocks, and vitamins or derivatives thereof. Color cosmetics such as foundations, blush, and eye shadows may contain one or more ingredients as for lotions, creams and moisturizers, and will contain a powder for coloration.

Particularly preferred compositions comprise:

(a) from about 5% to about 70% of a liquid insulating material;

(b) from about 5% to about 65% of a liquid conductive material;

(c) from about 0.5% to about 30% of a particulate material which is insoluble and immiscible in the composition; and optionally one or more of:

(d) from about 0% to about 20% of a structuring agent or thickener for stabilizing the composition;

(e) from about 0.1% to about 20% of an emulsifier; and (f) from about 0.5% to about 20% of a material for imparting wear or transfer resistance.

Methods of Use

Electrostatic Spray Techniques

The compositions hereof are suitably directly applied to the skin by electrostatic spray techniques. In general, this method involves raising the composition to be sprayed to a high electric potential in a spray nozzle to cause the composition to atomize as a spray of electrically charged droplets. The electrically charged droplets seek the closest earthed object to discharge their electric charge, which can be arranged to be the desired spray target.

For use in the present invention, the hardware and electrical componentry and circuitry may be of any suitable construction and design. The art of electrostatic spraying contains many examples of suitable apparatus which may be used in the present invention and such disclosures of such apparatus or particular features thereof may be applied either singly or in combination to the spray systems of the present invention. Examples of suitable electrostatic spraying hardware include those described in the following publications: U.S. Pat. Nos. 4,549,243; 4,561,037; 4,663,639; 4,854,506; 4,846,407; 5,121,884; 5,222,663; 5,222,664; 5,221,050; 5,290,600; 5,337,963; 5,292,067; 5,490,633; 5,184,778; 5,503,335; 5,684,666; and 4,776,515; Japanese patent No. 1,932,551; JP-A-56-97214; Canadian Patent Application No. 2018551-1; GB-A-1393333; GB-A-15697007; GB-A-2092025; GB-A-2061769; GB-A-2073052; Taiwanese Patent No. NI-64734; EPO Application No. 94924355.4 (Publication No. 716626); EPO Application No. 95915955.9 (Publication No. 748256); EPO Application No. 95916790.9 (Publication No. 748257); EPO Application No. 94931643.4 (Publication No. 789626); EPO Application No. 95932065.6 (Publication No. 776253); EPO Application No. 95932063.1 (Publication No. 785823); EP-A-029301; EP-A-253539; EP-A-224352; EP-A-031649; EP-A-132062; EP-A-163390; EP-A-171184; EP-A-234842; EP-A-243031; EP-A-368494; EP-A-441501; EP-A-468735; EP-A-468736; PCT Application No. GB96/01286 (Publication No. 096/40441); PCT Application No. GB97/00376 (Publication No. 097/31718); PCT Application No. GB97/02746; and WO-A-85/00761; all incorporated herein by reference in their entirety. Preferred electrostatic spray devices are disclosed in copending, commonly assigned U.S. patent application Ser. No. 09/377,333, entitled "Hand-Held Electrostatic Sprayer Apparatus" filed in the names of Chinto B. Gaw et al. on Aug. 18, 1999; and Ser. No. 09/377,332, entitled "Disposable Cartridge for Use in a Hand-Held Electrostatic Sprayer Apparatus" filed in the name of Chinto B. Gaw et al. on Aug. 18, 1999, both incorporated herein by reference.

Preferred devices include an apparatus suitable for small-scale personal use which has a reservoir for containing the topical composition, at least one delivery means, e.g., a nozzle, in communication with the reservoir; a high voltage generator generating voltage in the range of 1 to 26 kilovolts (e.g., from 12 to 26 kilovolts) powered from a portable or non-portable (preferably portable) electricity source; and control means for selectively applying the high voltage from the generator to the at least one delivery means. In use, the control means is actuated to electrostatically spray the topical composition from the at least one delivery means directly onto the skin at an intended site.

As will be appreciated by persons skilled in the art, particular constructional features and design and electrical and other operating parameters of such apparatuses may be selected or adjusted as necessary, in the context of the present invention, in accordance with the desired functioning characteristics, as for example dictated by the composition to be sprayed and/or the needs or wishes of a user. Features of the apparatus of the present invention which may be so selected and/or adjusted include for example: voltage generated by the high voltage generator and power source, electric field strength in or in the region of the product delivery means, flow rate of the product to be sprayed from the reservoir to and out of the delivery means, size and configuration of the delivery means itself and construction and properties of any product feed mechanism utilized between the reservoir and the output of the delivery means.

The size and configuration of the one or more delivery means in the apparatus of the invention may be of any suitable form and again may be selected in association with other parameters to give an optimized functioning electrostatic spray delivery system. Commonly the or each delivery means will be in the form of a nozzle, preferably of insulating or semi-insulating material such as plastics or various polymers, as is well known in the art. In one preferred form of nozzle, a conduit for carrying the product to be sprayed terminates in an orifice at the tip of the nozzle, from which orifice the product is ejected for example initially as a ligament but in any event eventually dispersing as a spray of charged droplets. The orifice preferably has a diameter of not greater than about 800 microns (e.g., from 508–762 microns or 0.020"–0.030"). Even more preferably the orifice has a diameter of from about 500 to about 750 microns.

The delivery means may advantageously include metering means to provide a dosing mechanism for delivering a predetermined fixed amount of material from the or each nozzle. Such an expedient may for example be useful in conjunction with a system having a controlled flow rate. In preferred embodiments of the apparatus of the invention, the or each delivery means is in communication, i.e. preferably fluid communication, with the reservoir or reservoirs (if for example more than one material or composition is to be desired to be sprayed from the same apparatus or even the same delivery means) by virtue of product feed means. In one preferred form, such feed means may comprise an insulator having a channel between the nozzle and the product reservoir, through which the product to be sprayed flows before reaching the point of high electric field strength where it is dispersed as a charged spray of droplets or particles. In another preferred form the feed means may comprise a hollow conduit through which the composition passes under the effect of capillary action.

As is well known in the art, the apparatus according to the invention preferably includes a trigger (i.e. a manual control means) or alternatively an automatic control means to selectively apply the high voltage from the generator to the or each delivery means to electrostatically spray the composition onto the skin. Any other suitable control means however, e.g. which automatically control actuation of the system, may be used, as will be appreciated by persons skilled in the art.

In preferred embodiments of the invention, voltages generated by the high voltage generator from the power source are in the range of from about 1 to about 26 kilovolts, more preferably from about 6 to about 20 kilovolts. The most suitable voltage for a given system may depend upon the product to be sprayed, as well as other parameters, all of which will generally be selected to give an overall optimized system. Voltage may be applied at constant positive or alternating polarity, however positive polarity is preferred.

Electric field strengths which are responsible for the spraying action of the electrostatic apparatus will be largely dependent upon the voltage applied. However, field strengths may be controlled or adjusted if necessary, for example by changes in nozzle configuration or geometry and/or the use of field intensifying electrodes, which are well known in the art cited above.

The deposition of the composition on the skin, including spray droplet size and spacing and skin coverage, is influenced by the product spray flow rate, the rate of product application to the skin, and the amount of product applied to the skin. In general, droplet size increases with increasing resistivity, decreasing voltage, and increasing flow rate, spacing increases with increasing voltage and decreasing deposition amount, and coverage increases with increasing flow rate and increasing deposition amount.

Optimum flow rates of material to be sprayed will generally depend upon the composition of the product itself, and may be selected appropriately on that basis preferably so as to avoid sensory negatives. Also, as already mentioned with respect to viscosity of the sprayable material, a suitable flow rate may be selected depending upon the particular delivery regime and/or habit or needs of a user. Generally it will be desired to utilize lower flow rates with concentrated materials in order to better control the deposition of the composition. By way of example, preferred flow rates of compositions for delivery in accordance with embodiments of the invention are in the range of from about 0.036 to about 1800 ml/hr (0.00001 to about 0.5 ml/sec), more preferably from about 0.1 to about 360 ml/hr (0.0001 to about 0.1 ml/sec), even more preferably from about 0.1 to 100 ml/hr, most preferably from about 1 to about 30 ml/hr per the delivery means. Particularly preferred applications utilize a higher speed flow rate of from about 4 to about 18 ml/hr (preferably about 9 ml/hr), and a lower speed flow rate of from about 2.4 to about 10.8 ml/hr (preferably about 7.2 ml/hr), where the low speed is about 0.2 to 0.8 times the high speed.

In general, as the flow rate increases it will be desired to utilize a higher voltage in order to provide optimal sprayability and small sprayed droplet sizes. In a preferred embodiment, the composition is sprayed at a flow rate of from about 0.1 to about 100 ml/hr, a voltage of from about 1 kV to about 26 kV (preferably about 1 kV to about 20 kV), and an application rate of from about 0.01 mg composition/$cm^2$ of skin to about 12 mg composition/$cm^2$ of skin. Relatively high solids compositions such as foundations are typically applied at a rate of about 1 mg/$cm^2$ skin; relatively low solids compositions such as skin lotions are typically applied at a rate of about 5 to 6 mg/$cm^2$ skin. Relatively low solids compositions such as skin lotions are typically delivered at a flow rate of from about 50 to about 60 ml/hr. Relatively high solids compositions such as foundations are preferably electrostatically sprayed at said application rate, at a flow rate of from about 1 to about 30 ml/hr and a voltage of from about 6 kV to about 20 kV. A voltage range of from about 3 kV to about 20 kV is preferred.

Total product application amounts, in terms of amount of product sprayed per $cm^2$ skin, is typically less than about 6 mg/$cm^2$. An exemplary application amount is about 0.8 mg/$cm^2$, which tends to provide about 30–40% skin coverage.

The product is typically applied at a rate of 0.005 sec/$cm^2$ skin area to 6 sec/$cm^2$ skin area, more preferably rate of 0.01 sec/$cm^2$ skin area to 3 sec/$cm^2$ skin area, most preferably rate of 0.05 sec/$cm^2$ skin area to 2 sec/$cm^2$ skin area.

Preferred Usage Instructions for Electrostatic Application

Electrostatic compositions may be applied by a second party (including robotic means) or the end-user of the composition. The present invention also relates to instructions for using an electrostatic spray device to apply topical compositions to the face, especially foundation compositions, and especially second-party and self-application techniques, context, and methods of training self-application.

a) Application Techniques

It has been found that improved results are achieved by observing certain directions relating to distance of the device (particularly the nozzle) from the target application area (the face), the rate of application of product to the skin (including flow rate and device speed settings), and motion of the device during application (including the direction and character of the motion).

In use, the device is held or otherwise positioned so as to efficiently deliver the spray to the target facial area and to avoid obstruction of the spray.

In general, the device is held or positioned sufficiently distant from the target such that the spray pattern spreads sufficiently and does not tend to form lines or other undesirable concentrated effects on the target substrate, and close enough such that the spray adequately grounds to the target so as to deliver optimum coverage and even-ness of laydown. Typically, the device is held or positioned such that the nozzle is from about 3–4 inches (9–13 cm) from the target facial area.

During self-application, it is best to keep one or both eyes open when applying to areas of the face below the nose, and closed when applying to areas of the face above the nose. When self-applying while the eyes are closed, it can be helpful to appropriately judge the distance with which to hold the device from the face, by first stretching the arm all the way out straight (until the feel of the spray mist on the face can no longer be felt clearly) and then bending the elbow to bring the device closer, slowly, until the spray mist is first clearly felt. This typically leads to ensuring that the device stays about 3–4 inches from the applier's face.

For improved even-ness of coverage, the device should be kept moving during application, preferably at a steady pace with a sweeping motion, without stopping in place while the device is operating. In general, the preferred pace is such that in one second one can usually transverse the forehead, or make two passes over a single cheek, depending on the facial size. The swath areas may be partially overlapped, such as occurs with a Zamboni smoothing ice. In a typical 60–90 second application, each facial area is typically passed over 2–8 times.

In a preferred technique, the composition is applied following the contours of the face and in four sections. First, smooth horizontal strokes are made across the forehead. Product is then applied to each side of the face utilizing back and forth sweeping, semi-circular motions following the natural contours of the cheekbone working down to the chin from the side of the face to the center of the face. While applying to the cheeks, it is important to avoid the fourth region, the nose, which is preferably sprayed last since its relative height tends to preferably attract spray. The nose is then sprayed, if needed, along with the area above the upper lip. Where the wearer has visible facial hair, it may be preferred to tilt the nozzle slightly downward to minimize accentuating the visibility of the hair. Also, when first self-applying it is preferred to begin with the jaw line and work "up" the face until one becomes more comfortable with the application process. This allows the wearer to keep her eyes open initially and see where the spray is going on the face, and helps for judging how far away from the face she may be with the device.

Improved results have also been found where the applicant utilizes two or more speeds such as described above for applying the product. The preferred use is typically to use a faster speed (higher flow rate) for all-over-face coverage and a slower speed for spot coverage. Preferred is a higher speed flow rate of from about 4 to about 18 ml/hr (preferably about 9 ml/hr), and a lower speed flow rate of from about 2.4 to about 10.8 ml/hr (preferably about 7.2 ml/hr), where the low speed is about 0.2 to 0.8 times the high speed The slow speed allows a more controlled build up of coverage in a specified area without unintentional overapplication. In general, the application process is designed so as to avoid overapplication, resulting in an unnatural look and/or uneven application, but to provide sufficient coverage. It can be helpful for a second party to first view the user with their typical facial makeup in order to identify likely coverage objectives. It is also helpful to utilize a stepwise application, involving at least one sequence of overall application and optionally spot coverage, so that the applicant or user can titrate to the desired appearance.

A typical application process involves the following steps:

1) Apply all over the face using a relatively fast speed/flow rate designed to apply product at a rate of about 9 milliliters/hour;
2) judge whether or not more coverage is needed, and if so where and how much more;
3a) If more product is desired in "spot" areas, e.g., age spots, acne, red areas, dark areas, apply additional spray to the specific areas defined using a slow speed/flow rate designed to apply about 5–7 milliliters/hour;
3b) If more product is desired "all-over", repeat step (1);
4) Iterate Steps 2 and 3 until the desired coverage is obtained.

The overall time for application tends to be from about 0.5 to 3 minutes (generally from about 60 to about 90 seconds).

b) Context

When instructing someone to apply product either to themselves or others, it has been found that the context with which the first application or demonstration is made is very important to help the end-user feel comfortable and positive about the application experience. The context is preferably designed to provide the user with visible and tactile expectations. It preferably includes the steps of reviewing safety, explaining how the spray works, and demonstrating how the spray works.

More particularly, the safety of the composition, device and method is reviewed, typically including a recommendation to keep eyes closed when spraying above the nostrils as an added safety level. Any eye, inhalation, grounding/electrical safety or other concerns which the user may have are addressed.

How the spray works is generally explained, for example, by explaining that the product is a fine mist of product droplets that are charged so that they stay separated during application and are uniquely attracted to the face versus non-target areas such as the hair, clothing, etc., yet needs no blending. Demonstrating how the spray works preferably includes showing how to hold the device (e.g., by resting it between the thumb and fore finger), and how to activate the device (e.g., by pressing the on/off button with your forefinger, preferably instructing to keep fingers away from the nozzle. A useful demonstration before actual use involves providing a visible expectation (i.e., how the product comes out of the device), e.g., by spraying on a piece of paper, paper towel, non-target skin (e.g, hand or arm) or the like, and providing a tactile expectation, e.g., by spraying on non-target skin to show how the spray feels on the skin. The user should understand that the product is emitted as a fine, uniform spray or mist that needs no blending into the skin, which is very light in feel. The user should also preferably understand that the mist generally forms a circular, versus linear (jets) pattern and that the swath diameter is proportional to the distance of the device from the face.

Other means may be provided to enhance the user's experience, e.g., music or other audio effects, flowers, aromatherapy, massage, or other known means of promoting relaxation.

c) Self-Application Training

Where the user intends to self-apply the product, the learning curve for self-applying the composition is also important to user satisfaction. Preferred training involves at least a step of joint application by the user and a second party. More preferred training methods allow the user to gradually become familiar with the techniques, and involve a sequence of steps comprising application by a second party, joint application by the user and a second party, and full application by the user with optional assistance of a second party or instructional materials. The steps are preferably performed on different days, more preferably on consecutive days. However, the steps may be performed on the same day and optionally immediately following each other if it is practical and provided that cleansing of the user's skin between steps does not cause negative effects.

One preferred method of training is a 3–5 day training period during which the user gradually becomes comfortable with self-application:

(1) On the first day, a second party applies the product to the end-user.
(2) On the second day, the second party applies product to half the end-user's face and then the end-user completes the application with personalized guidance from the second party and/or instructional aids such as a usage pamphlet and/or a video of others self-applying the product. The second party or instructional aid preferably reminds the end user of the proper device distance, speed, the desirability of keeping the eyes closed as described above, and other helpful suggestions such as described above, e.g., such as beginning with the jaw line and working "up" the face until becoming more comfortable with the application process.
(3) On the third day, the end-user applies full face product with optional guidance from the second party and/or instructional materials.
(4) On optional fourth and fifth days, the third day procedure is repeated.

When it is desirable to demonstrate self-application with a single demonstration, the preferred method is to follow the above instructions for the second day.

The self-application learning curve preferably involves three elements of expectation or context, technique or application, and confidence. Expectation/context involves addressing any safety concerns and describing the product which comes out of the device. Technique/application involves application techniques, including how to hold/handle the device and instructions regarding proper distance from the face, amount of product to apply, how long to apply, hand motion, and application speeds. Confidence involves allowing the user to practice applying the product, optionally with assistance from a second party or other instructional aids. Preferred aspects of these elements is as described herein above.

Other Topical Application Methods

The topical compositions can alternatively be applied to the skin to form the discontinuous films by silk screen techniques or the like, and additionally by using application techniques which provide product deposition via the use of normal forces (i.e., forces perpendicular to skin surface).

In the first method, a piece of plastic, metal, cloth or other mesh (preferably conformable to facial contours), with evenly spaced holes/pores of about 150 microns or less in diameter is placed against the skin. Then topical composition, e.g., a pigmented foundation, is pressed through the holes in the mesh to deposit the same pattern of droplets on the skin which exists in the pores of the mesh. One convenient way to press the fluid through the mesh is to first absorb it into a sponge, cloth or other absorbent material and then to press the soaked sponge or other material against the mesh. Another means of accomplishing this is to spread or draw the fluid across the mesh with a stiff-edged product such as a rubber squeegee, much like spackling a wall. After the product is pressed through the mesh, the mesh is removed, and cleaned if desired for re-use. The mesh is then moved to any bordering, uncovered areas and the process is repeated as many times as necessary to complete application of the target area. Once the fluid on the skin has dried, if applicable, the process may be repeated by placing the mesh back over the areas where product is already deposited, and orienting the mesh at a different angle to minimize the potential for overlapping droplets. This re-application process will allow for tighter particle spacing than inherently exists in the mesh, if desired.

Any type mesh which allows for a deposition with the desirable size and spacing pattern described herein may be used. Examples of such materials include microaperatured formed films as are described in U.S. Pat. No. 4,342,314, issued to Radel et al. on Aug. 3, 1982 and U.S. Pat. No. 4,629,643 issued to Curro et al. on Dec. 16, 1986, both of which are herein incorporated by reference in their entirety. As is described in these references, suitable materials for these formed films are preferably polyolefins, e.g., polyester. Preferable mesh hole size and spacing is equivalent to the desired end discontinuous film particle size and spacing.

Alternatively, the discontinuous deposition pattern is achieved without the use of a mesh or screen, but rather is accomplished through the use of a porous material with pores which are less than about 150 microns in diameter. The porous structure may comprise open cells, closed cells, or some combination thereof. The term "cells", as used herein, refers to the 3-dimensional voids present in the material which may, or may not have interstitial openings which would connect the voids to one another. In one embodiment, the fluid topical skin product is absorbed into the porous material and then "blotted" onto the skin using forces perpendicular to the skin (as opposed to tangential, or shearing forces). This application technique uses the pore size and pore spacing of the material to create the discontinuous deposition pattern.

Such porous materials can be created by techniques which include, but are not limited to:

1) seeding mechanisms in which the pores are created by incorporating a physical material which is later extracted, destroyed, removed, or decays after the structure is formed, examples of such materials include elastomeric rubber structures manufactured by the Porelon and MicroFoam Companies such as Porlon and Microfoam brand materials which are described in U.S. Pat. Nos. 3,971,315 and 4,824,621, both of which are herein incorporated by reference in their entirety;

2) aerating (i.e., incorporating air or inert gases into) polymeric materials via mechanical shearing, high pressure (e.g., forced air), or the like, examples include foams of synthetic latex nitrites produced Latex Foam Products, Inc. (LFP) such as "NBR", "SBR", or "SK" type materials;

3) using emulsion chemistry and processing techniques to control the pore size and density—examples of such materials include polyurethane foams produced by the Lendell corporation, or flexible microcellular foams such as those cited in U.S. Pat. Nos. 5,260,345 and 4,522,953, both of which are herein incorporated by reference in their entirety.

4) sintering powder particulates of various sizes to create the desired pore size and density—examples of such materials which utilize particulates of high density polyethylene, polypropylene, or nylon and are produced by the Porex Technologies Corporation (e.g. Porex X4900 and X4800 series in coarse sheets or custom-molded parts).

In another variation on the use of porous materials to create a discontinuous pattern, a continuous or discontinuous film of fluid is applied to the skin and the porous material (as described above) is subsequently blotted onto the continuous film to remove fluid from the skin surface by absorbing the fluid into the pores of the material. The discontinuous pattern, in this case, is formed by and corresponds to the structural pattern of the polymeric material which separates the pores. In this example, the spacing of polymeric material which separates the pores should be less than 150 microns in effective diameter. The phrase "effective diameter", as used herein, refers to the diameter of a circle with an area equal to the area of the irregularly shaped region of interest.

In yet another execution, the discontinuous pattern is created by blotting non-porous materials with a relief texture in which the raised areas of the texture do not exceed 150 microns in effective diameter. In this execution the nonporous, textured material is blotted into a fluid reservoir (much like an ink pad), imparting the fluid product onto the raised textured areas of the non-porous substrate. The substrate is then blotted onto the skin (using forces normal to the skin) and the raised textured pattern of the nonporous material is transferred to the skin surface.

In still another execution, the discontinuous pattern is created by blotting non-porous materials with a relief texture where the reliefed areas of the texture do not exceed 150 microns in effective diameter. The phrase relief texture or reliefed areas, as used herein, refers to the depressed areas of the textured surface or textures formed by such depressed areas or regions. In this execution the nonporous, textured material is blotted into a fluid reservoir, imparting the fluid product onto all surfaces of the substrate (both raised and depressed). The fluid product on the raised areas is then removed through a secondary process such wiping, absorbing, evaporating, or the like. The substrate is then blotted onto the skin (using forces normal to the skin) and the depressed textured pattern of the nonporous material is transferred to the skin surface.

EXAMPLES

The following examples are representative but non-limiting of the invention.

Examples 1–5

Cosmetic foundations are made by combining the following ingredients:

| Ingredient | Ex 1 | Ex 2 | Ex 3 | Ex 4 | Ex 5 |
|---|---|---|---|---|---|
| Group A: | | | | | |
| Cyclomethicone 245 | 15.22 | 15.81 | 17.9 | 15.22 | 13.22 |
| Cyclomethicone & Dimethicone Copolyol | 10.40 | 11.46 | 10.74 | 10.40 | 10.40 |
| Cetyl Dimethicone Copolymer | 0.50 | 0.50 | 0.52 | 0.5 | 0.5 |
| Group B: | | | | | |
| Titanium Dioxide - Dimethicone Treated | 5.35 | 12.03 | 5.51 | 5.35 | 5.35 |
| Yellow Iron Oxide | 0.64 | 2.45 | 0.65 | 0.64 | 0.64 |
| Red Iron Oxide | 0.13 | 0.50 | 0.14 | 0.13 | 0.13 |
| Black Iron Oxide | 0.08 | 0.09 | 0.08 | 0.08 | 0.08 |
| Micronized Titanium Dioxide | 0.16 | 0.79 | 0.17 | 0.16 | 0.16 |
| Ethylene Acrylates Copolymer[1] | 3.00 | 3 | 3.09 | 3 | 3 |
| Boron Nitride UHP 11072[2] | 3.00 | 3 | 3.09 | 3 | 3 |
| Talc - Dimethicone Treated | 3.03 | 4.37 | 3.13 | 3.02 | 3.02 |
| Group C: | | | | | |
| Organosiloxane resin[3] | 3.00 | 3 | 3 | 3 | 10 |
| Group D: | | | | | |
| Propylene Glycol | 55.50 | 43 | 52 | 55.17 | 50.5 |
| Sodium Chloride | — | — | — | 0.33 | — |

[1]Ethylene Acrylates Copolymer available as EA-209 from Kobo Products.
[2]Boron Nitride UHP 1107 grade available from Carborundum.
[3]MQ Resin (0.7:1 ratio M:Q) available as SR 1000 from General Electric.

Combine the Group A ingredients and mix well with a homogenizer set at 2000–4000 rpm. Add the Group B ingredients. During addition mix at 5000–7500 rpm, when addition is complete set mixing speed to 8000–10000 rpm. Do not let temperature rise above 40 C during mixing. After 30 minutes of mixing check the particle size with a Hegman gauge or glass slides. If the sample has an acceptable particle size (i.e. less than 30 microns), mix in Part C at a mixing speed of 5000–7500 rpm. Keep temperature in 20 C–40 C range. Assist with hand mixing if necessary. After 15 minutes of mixing, raise mixing speed to 7500–10000 rpm. Slowly add Part D ingredients at a rate of 30–40 g/minute. Keep the temperature at 45 C or less (ideally temperature should be from 20–40 C). After addition is complete mix at 5000 rpm–7500 rpm for about 10 minutes. After 10 minutes allow to reach ambient conditions and pour into appropriate container.

Examples 6–13

Cosmetic foundations are made by combining the following ingredients:

| Ingredient | Ex 6 | Ex 7 | Ex 8 | Ex 9 | Ex 10 | Ex 11 | Ex 12 | Ex 13 |
|---|---|---|---|---|---|---|---|---|
| Group A: | | | | | | | | |
| Cyclomethicone 245 | 15.25 | 13.3 | 35.37 | 30.4 | 15 | — | — | — |
| Cyclomethicone & Dimethicone Copolyol | 10.44 | 10.44 | 15.44 | 10.44 | 9 | — | — | — |
| Cetyl Dimethicone Copolymer | 0.50 | 0.50 | 0.50 | 0.50 | — | — | — | — |
| Isododecane | — | — | — | — | — | 24.25 | 21.69 | 29.65 |
| Arlacel P135 surfactant (ICI) | — | — | — | — | — | 4.75 | 4.5 | 4.5 |
| Group B: | | | | | | | | |
| Titanium Dioxide - Dimethicone Treated | 5.35 | 5.35 | 5.35 | 5.35 | — | — | 5.35 | 5.35 |
| Yellow Iron Oxide | 0.9 | 0.9 | 0.9 | 0.9 | 0.19 | 0.19 | 0.9 | 0.9 |
| Red Iron Oxide | 0.18 | 0.18 | 0.18 | 0.18 | 1.24 | 1.24 | 0.18 | 0.18 |
| Black Iron Oxide | 0.05 | 0.05 | 0.05 | 0.05 | — | — | 0.05 | 0.05 |
| Micronized Titanium Dioxide | 0.16 | 0.16 | 0.16 | 0.16 | — | — | 0.16 | 0.16 |
| Ethylene Acrylates Copolymer[1] | 2.94 | 2.96 | 2.94 | 2.94 | 6 | 6 | 2.94 | 2.94 |
| Boron Nitride UHP 11072[2] | 2.94 | 2.94 | 2.95 | 2.94 | 6 | 6 | 2.94 | 2.94 |
| Talc - Dimethicone Treated | 1.33 | 0.95 | 1.22 | 1.21 | — | — | 1.33 | 1.33 |
| Red #7 Ca lake | — | — | — | — | 0.87 | 0.87 | — | — |
| Red #6 Ba lake | — | — | — | — | 0.52 | 0.52 | — | — |
| Blue #1 Al lake | — | — | — | — | 0.24 | 0.24 | — | — |
| Group C: | | | | | | | | |
| Organosiloxane resin[3] | 2.94 | 2.94 | 2.94 | 2.93 | 2.94 | 2.94 | 2.96 | — |
| Group D: | | | | | | | | |
| Compritol 888 ATO (glyceryl behenate) | 2 | — | 2 | 2 | 3 | 3 | 2 | 2 |
| Dow Corning 9040 silicone gel thickener | — | 9.33 | — | — | — | — | — | — |
| Group E: | | | | | | | | |
| Propylene Glycol | 55 | 50 | 30 | 40 | 55 | 50 | 55 | 50 |

[1]Ethylene Acrylates Copolymer available as EA-209 from Kobo Products.
[2]Boron Nitride UHP 1107 grade available from Carborundum.
[3]MQ Resin (0.7:1 ratio M:Q) available as SR 1000 from General Electric.

Combine Group A ingredients and mix well with a homogenizer set at 2000–4000 rpm. Add Group B ingredients. During addition mix at 5000–7500 rpm, when addition complete set mixing speed to 8000–10000 rpm. Do not let temperature rise above 40 C during mixing. After 30 minutes of mixing check particle size with Hegman gauge or glass slides. If the sample has an acceptable particle size (i.e. less than 30 microns), raise mixing speed to 7500–10000 rpm. Slowly add Part C. After 15 minutes of mixing at 5000–7500 rpm, raise the temperature slowly to 35–40 C. When the temperature has equilibrated, slowly add Part D. The mixing speed should be 5000–7500 rpm for 10 minutes. Slowly decrease temperature to 20 C–35 C, then raise mixing speed to 7500–10000 rpm. Add Part E at approximately 30–40 g/minute. Keep the temperature at 45 C or less (ideally temperature should be from 20–40 C). After addition is complete mix at 5000 rpm–7500 rpm for about 10 minutes. After 10 minutes allow to reach ambient conditions and pour into appropriate container.

Example 14

A cosmetic blush is made by combining the following ingredients:

| Ingredient | Ex 14 |
|---|---|
| Group A: | |
| Cyclomethicone 245 | 19.89 |
| Cyclomethicone & Dimethicone Copolyol | 10.44 |
| Cetyl Dimethicone Copolymer | 0.50 |
| Group B: | |
| Ethylene Acrylates Copolymer[1] | 2.94 |
| Boron Nitride UHP 11072[2] | 2.96 |
| Talc - Dimethicone Treated | 1.33 |
| Red 6 Ca Lake | 2 |
| Group C: | |
| Organosiloxane resin[3] | 2.94 |
| Group D: | |
| Compritol 888 ATO (glyceryl behenate) | 2 |
| Group E: | |
| Propylene Glycol | 55 |

[1]Ethylene Acrylates Copolymer available as EA-209 from Kobo Products.
[2]Boron Nitride UHP 1107 grade available from Carborundum.
[3]MQ Resin (0.7:1 ratio M:Q) available as SR 1000 from General Electric.

Prepare as for Examples 6–13.

Example 15

A spray useful for preventing or reducing skin shine is made by combining the following ingredients:

| Ingredient | Ex 15 |
|---|---|
| Group A: | |
| Cyclomethicone 245 | 21.89 |
| Cyclomethicone & Dimethicone Copolyol | 10.44 |
| Cetyl Dimethicone Copolymer | 0.50 |
| Group B: | |
| Ethylene Acrylates Copolymer[1] | 2.94 |
| Boron Nitride UHP 11072[2] | 2.94 |
| Talc - Dimethicone Treated | 1.33 |

-continued

| Ingredient | Ex 15 |
|---|---|
| Group C: | |
| Organosiloxane resin[3] | 2.96 |
| Group D: | |
| Compritol 888 ATO (glyceryl behenate) | 2 |
| Group E: | |
| Propylene Glycol | 55 |

[1]Ethylene Acrylates Copolymer available as EA-209 from Kobo Products.
[2]Boron Nitride UHP 1107 grade available from Carborundum.
[3]MQ Resin (0.7:1 ratio M:Q) available as SR 1000 from General Electric.

Prepare as for Examples 6–13.

Example 16

A topical composition for improving skin texture (e.g., reducing the visibility of lines, wrinkles) is made by combining the following ingredients:

| Ingredient | Ex 16 |
|---|---|
| Group A: | |
| isododecane | 28 |
| Arlacel P135 surfactant | 4.75 |
| Group B: | |
| Coslin C-100 (Englehard) | 4 |
| Group C: | |
| Organosiloxane resin[1] | 3.00 |
| Group D: | |
| Propylene Glycol | 60.25 |

[1]MQ Resin (0.7:1 ratio M:Q) available as SR 1000 from General Electric.

Prepare as for Examples 1–5.

The products of Examples 1–16 are electrostatically sprayed to the face in accordance with the description herein.

What is claimed is:

1. A method of topically applying a topical emulsion composition formed prior to spraying comprising electrostatically spraying the emulsion composition onto the skin, wherein the emulsion comprises:

a) from about 5% to about 75% of an insulating external phase comprising one or more liquid insulating materials; and b) from about 15% to about 80% of a conductive internal phase comprising one or more conductive materials, wherein the topical emulsion composition is a two-phase composition that does not form electrical continuity between the insulating external phase and the conductive internal phase.

2. A method according to claim 1 wherein the composition comprises from about 15% to about 70% of the insulating external phase and from about 20% to about 75% of the conductive internal phase.

3. A method according to claim 1 wherein the composition comprises from about 20% to about 60% of the insulating external phase and from about 30% to about 70% of the conductive internal phase.

4. A method according to claim 1 wherein the weight ratio of insulating external phase to conductive internal phase is about 0.2:1 to 8:1.

5. A method according to claim 1 wherein the insulating external phase has a viscosity of about 10,000 cSt or less.

6. A method according to claim 1 wherein the insulating material of the external phase is selected from the group consisting of volatile silicones, volatile hydrocarbons, and mixtures thereof.

7. A method according to claim 6 wherein the insulating material comprises a cyclic polyalkylsiloxane having the formula $[SiR_2—O]_n$ wherein R is methyl and n is an integer of from about 4 to about 6.

8. A method according to claim 6 wherein the insulating material comprises $C_8$ to $C_{20}$ isoparaffin.

9. A method according to claim 8 wherein the isoparaffin is isododecane, isohexadecane isoeicosane, or a mixture thereof.

10. A method according to any of the preceding claims wherein the conductive internal phase comprises one or more liquid conductive materials.

11. A method according to claim 10 wherein the conductive material of the internal phase is selected from the group consisting of water, alcohols, glycols, polyols, ketones and mixtures thereof.

12. A method according to claim 10 wherein the conductive material of the internal phase is selected from the group consisting of alcohols, glycols, polyols and mixtures thereof.

13. A method according to claim 10 wherein the conductive material of the internal phase is selected from the group consisting of propylene glycol, butylene glycol, dipropylene glycol, phenyl ethyl alcohol, ethanol, isopropyl alcohol, glycerin, 1,3-butanediol, 1,2-propane diol, isoprene glycol, water, acetone, and mixtures thereof.

14. A method according to claim 10 wherein the conductive material of the internal phase is selected from the group consisting of propylene glycol, butylene glycol, ethanol, glycerin, water, and mixtures thereof.

15. A method according to claim 10 wherein the conductive material of the internal phase is selected from the group consisting of propylene glycol, ethanol, and mixtures thereof.

16. A method according to claim 10 wherein the conductive material of the internal phase is propylene glycol.

17. A method according to claim 1 wherein the composition comprises about 35 weight % or less solids.

18. A method according to claim 1 wherein the composition comprises one or more ingredients selected from the group consisting of materials which impart film forming or substantive properties, powders, skin feel ingredients, emulsifiers, and structuring or thickening agents.

19. A method according to claim 1 wherein the composition is a cosmetic foundation.

20. A method according to claim 1 wherein the composition is electrostatically sprayed at a flow rate of from about 0.1 to about 100 ml/hr, a voltage of from about 1 kV to about 20 kV, and an application rate of from about 0.01 mg composition/$cm^2$ skin to about 12 mg composition/$cm^2$ skin.

21. A method according to claim 20 wherein the composition is electrostatically sprayed at a flow rate of from about 1 to about 30 ml/hr and a voltage of from about 6 kV to about 20 kV.

* * * * *